US012596132B2

(12) United States Patent
Wissmann et al.

(10) Patent No.: US 12,596,132 B2
(45) Date of Patent: Apr. 7, 2026

(54) METHODS AND APPARATUS FOR ASCERTAINING SPECIMEN AND/OR SPECIMEN CONTAINER CHARACTERISTICS

(71) Applicant: Siemens Healthcare Diagnostics Inc., Tarrytown, NY (US)

(72) Inventors: Patrick Wissmann, Munich (DE); Benjamin S. Pollack, Jersey City, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1442 days.

(21) Appl. No.: 16/635,537

(22) PCT Filed: Jul. 25, 2018

(86) PCT No.: PCT/US2018/043758
§ 371 (c)(1),
(2) Date: Jan. 30, 2020

(87) PCT Pub. No.: WO2019/027770
PCT Pub. Date: Feb. 7, 2019

(65) Prior Publication Data
US 2020/0256885 A1 Aug. 13, 2020

Related U.S. Application Data

(60) Provisional application No. 62/538,939, filed on Jul. 31, 2017.

(51) Int. Cl.
*G01N 35/04* (2006.01)
*G01N 21/25* (2006.01)
(Continued)

(52) U.S. Cl.
CPC ........... *G01N 35/04* (2013.01); *G01N 21/253* (2013.01); *G01N 21/31* (2013.01); *G01N 33/487* (2013.01);
(Continued)

(58) Field of Classification Search
CPC ...... G01N 35/04; G01N 21/253; G01N 21/31; G01N 33/487; G01N 35/00732;
(Continued)

(56) References Cited

U.S. PATENT DOCUMENTS 6,353,471 B1 3/2002 Samsoondar et al.
7,422,693 B2 9/2008 Carter et al.
(Continued)

FOREIGN PATENT DOCUMENTS

CN 2576233 Y 10/2003
CN 104502285 A 4/2015
(Continued)

OTHER PUBLICATIONS

Machine translation of JP H0783831 A (Year: 1995).*
(Continued)

*Primary Examiner* — Elizabeth A Robinson
*Assistant Examiner* — Sophia Y Lyle

(57) ABSTRACT

An optical characterization apparatus for imaging a specimen container containing a specimen. The optical characterization apparatus includes a moveable hood configured to move between an open state and a closed state relative to a specimen container imaging location and having an interior, wherein when the moveable hood is in the closed state, a specimen container positioned at the specimen container imaging location is at least partially located within the interior of the moveable hood. One or more optical devices coupled to or within the interior of the moveable hood are positioned, when the moveable hood is in the closed state, to (Continued)

allow imaging of a specimen container positioned at the specimen container imaging location. Automated specimen testing systems, optical characterization apparatus, and methods of measuring characteristics of specimen containers are provided, as are other aspects.

21 Claims, 9 Drawing Sheets

(51) Int. Cl.

| | |
|---|---|
| *G01N 21/31* | (2006.01) |
| *G01N 33/487* | (2006.01) |
| *G01N 35/00* | (2006.01) |
| *G01N 21/84* | (2006.01) |

(52) U.S. Cl.

CPC . *G01N 35/00732* (2013.01); *G01N 2021/845* (2013.01); *G01N 2035/00752* (2013.01); *G01N 2035/0403* (2013.01); *G01N 2201/0627* (2013.01)

(58) Field of Classification Search

CPC ... G01N 2021/845; G01N 2035/00752; G01N 2035/0403; G01N 2201/0627; G01N 2201/064; G01N 2201/101

See application file for complete search history.

(56) References Cited

U.S. PATENT DOCUMENTS

| | | | |
|---|---|---|---|
| 7,663,738 | B2 | 2/2010 | Johansson |
| 7,760,340 | B2 | 7/2010 | Hoshiko et al. |
| 7,771,659 | B2 | 8/2010 | Ziegler |
| 7,854,891 | B2 | 12/2010 | Yamamoto et al. |
| 7,982,201 | B2 | 7/2011 | Bryant et al. |
| 8,064,061 | B2 | 11/2011 | Yamamoto et al. |
| 8,194,235 | B2 | 6/2012 | Kosaka et al. |
| 8,380,444 | B2 | 2/2013 | Kim et al. |
| 8,381,581 | B2 | 2/2013 | Walsh et al. |
| 8,545,760 | B2 | 10/2013 | Yamamoto et al. |
| 8,859,289 | B2 | 10/2014 | Marty et al. |
| 10,816,538 | B2 | 10/2020 | Kluckner et al. |
| 10,928,310 | B2 | 2/2021 | Wissmann et al. |
| 11,073,472 | B2 | 7/2021 | Wissmann et al. |
| 11,333,553 | B2 | 5/2022 | Wissmann et al. |
| 11,538,159 | B2 | 12/2022 | Kluckner et al. |
| 11,815,446 | B2 | 11/2023 | Wissmann et al. |
| 11,815,519 | B2 | 11/2023 | Wissmann et al. |

| | | | | |
|---|---|---|---|---|
| 2001/0004285 | A1 | 6/2001 | Cadell et al. | |
| 2004/0168919 | A1 | 9/2004 | Kurt et al. | |
| 2006/0250517 | A1* | 11/2006 | Nilson | G01N 21/763 |
| | | | | 348/370 |
| 2008/0261294 | A1 | 10/2008 | Noda et al. | |
| 2009/0049933 | A1* | 2/2009 | Decaux | B01L 9/56 |
| | | | | 73/863.01 |
| 2010/0085429 | A1 | 4/2010 | Terje et al. | |
| 2011/0076199 | A1* | 3/2011 | Meller | G01N 21/255 |
| | | | | 356/440 |
| 2011/0228143 | A1* | 9/2011 | Makino | H04N 23/73 |
| | | | | 348/E9.037 |
| 2011/0267450 | A1 | 11/2011 | Pronkine | |
| 2012/0140230 | A1 | 6/2012 | Miller | |
| 2013/0076882 | A1 | 3/2013 | Itoh | |
| 2013/0240754 | A1* | 9/2013 | Iguchi | G01N 21/645 |
| | | | | 250/228 |
| 2014/0293036 | A1 | 10/2014 | Ddecaux et al. | |
| 2015/0008339 | A1* | 1/2015 | French | G01N 21/6456 |
| | | | | 250/458.1 |
| 2015/0241457 | A1 | 8/2015 | Miller | |
| 2016/0138071 | A1 | 5/2016 | Edberg | |
| 2018/0045654 | A1* | 2/2018 | Park | G01N 21/25 |

FOREIGN PATENT DOCUMENTS

| | | |
|---|---|---|
| CN | 105917352 A | 8/2016 |
| DE | 10 2014 216 576 A1 | 2/2016 |
| EP | 1186893 B1 | 1/2008 |
| EP | 1967840 A2 | 9/2008 |
| JP | H02-116742 A | 5/1990 |
| JP | H02-114993 U | 9/1990 |
| JP | H04-071168 U | 6/1992 |
| JP | H07 83831 A | 3/1995 |
| JP | 2500722 Y2 | 3/1996 |
| JP | H09-169392 A | 6/1997 |
| JP | 2008-268019 A | 11/2008 |
| JP | 2010-525342 A | 7/2010 |
| JP | 2011-075560 A | 4/2011 |
| WO | 0036400 A1 | 6/2000 |
| WO | 2012/073568 A | 6/2012 |
| WO | 2016/052704 A1 | 4/2016 |
| WO | 2016/133900 A1 | 8/2016 |

OTHER PUBLICATIONS

PCT International Search Report and Written Opinion dated Nov. 9, 2018 (9 Pages).

Extended EP Search Report dated Jul. 6, 2020 of corresponding European Application No. 18841118.5, 4 Pages.

\* cited by examiner

900

Enclosing at Least a Portion of a Sample Container With a Hood — 902

Rotating One or More Optical Devices Located Within the Hood at Least Partially Around the Sample Container — 904

Generating Image Data of the Sample Container Using the One or More Optical Devices — 906

METHODS AND APPARATUS FOR ASCERTAINING SPECIMEN AND/OR SPECIMEN CONTAINER CHARACTERISTICS

This application claims priority to U.S. provisional application Ser. No. 62/538,939 filed on Jul. 31, 2017, the contents of which is incorporated herein by reference in its entirety.

FIELD

The present disclosure relates to methods and apparatus for determining characteristics of a specimen container and/or its contents.

BACKGROUND

A wide variety of automated chemical analyzers are used to analyze patient specimens. One such analyzer is a tube characterization station (TCS) that analyzes specimen containers and/or their contents. A TCS may back illuminate a specimen container and capture an image of the specimen container and its contents using a camera. The captured image is analyzed to provide information about the specimen container and/or the contents therein. Some TCSs employ several cameras and backlights to capture images of specimen containers and their contents from different angles or viewpoints. For example, a track may move specimen containers to a fixed imaging location surrounded by several cameras that capture several images of the specimen containers and/or their contents.

A TCS typically has a large footprint. For example, a TCS may include three cameras and three backlights surrounding an imaging location. In addition, the TCS may include a track or other device that transports specimen containers into and out of the imaging location. When a TCS is incorporated into a large chemical test station, the aforementioned components may consume a large portion of the area of the chemical test station. In addition to the large footprint, it is difficult to keep stray light that may affect captured images of the specimen containers and their contents from the imaging location during imaging.

Accordingly, improved systems, apparatus, and methods for imaging specimen containers and their contents are desired.

SUMMARY

In one aspect, a method of imaging a specimen container and/or a specimen in a specimen container is provided. The method includes enclosing at least a portion of a specimen container with a moveable hood, rotating one or more optical devices located within the moveable hood at least partially around the specimen container, and generating image data of the specimen container using the one or more optical devices.

In another aspect, an optical characterization station is provided. The optical characterization station includes a moveable hood configured to move between an open state and a closed state relative to a specimen container imaging location and having an interior, wherein when the moveable hood is in the closed state, a specimen container positioned at the specimen container imaging location is at least partially located within the interior of moveable hood, and one or more optical devices affixed to or within the moveable hood and positioned, when the moveable hood is in the closed state, to allow imaging of a specimen container positioned at the specimen container imaging location.

In another aspect, an automated specimen testing system is provided. The automated specimen testing system includes a track configured to move a specimen container to an imaging location, a moveable hood configured to move between an open state and a closed state relative to a specimen container imaging location and having an interior, wherein when the moveable hood is in the closed state, a specimen container positioned at the specimen container imaging location is at least partially located within the interior of moveable hood, and one or more optical devices within the interior of the moveable hood and positioned, when the moveable hood is in the closed state, to allow imaging of a specimen container positioned at the specimen container imaging location.

Numerous other aspects are provided in accordance with these and other embodiments of the disclosure. Other features and aspects of embodiments of the disclosure will become more fully apparent from the following detailed description, the claims, and the accompanying drawings.

BRIEF DESCRIPTION OF THE FIGURES

The drawings, described below, are for illustrative purposes only and are not necessarily drawn to scale. The drawings are not intended to limit the scope of the disclosure in any way.

DETAILED DESCRIPTION

Figure 1:
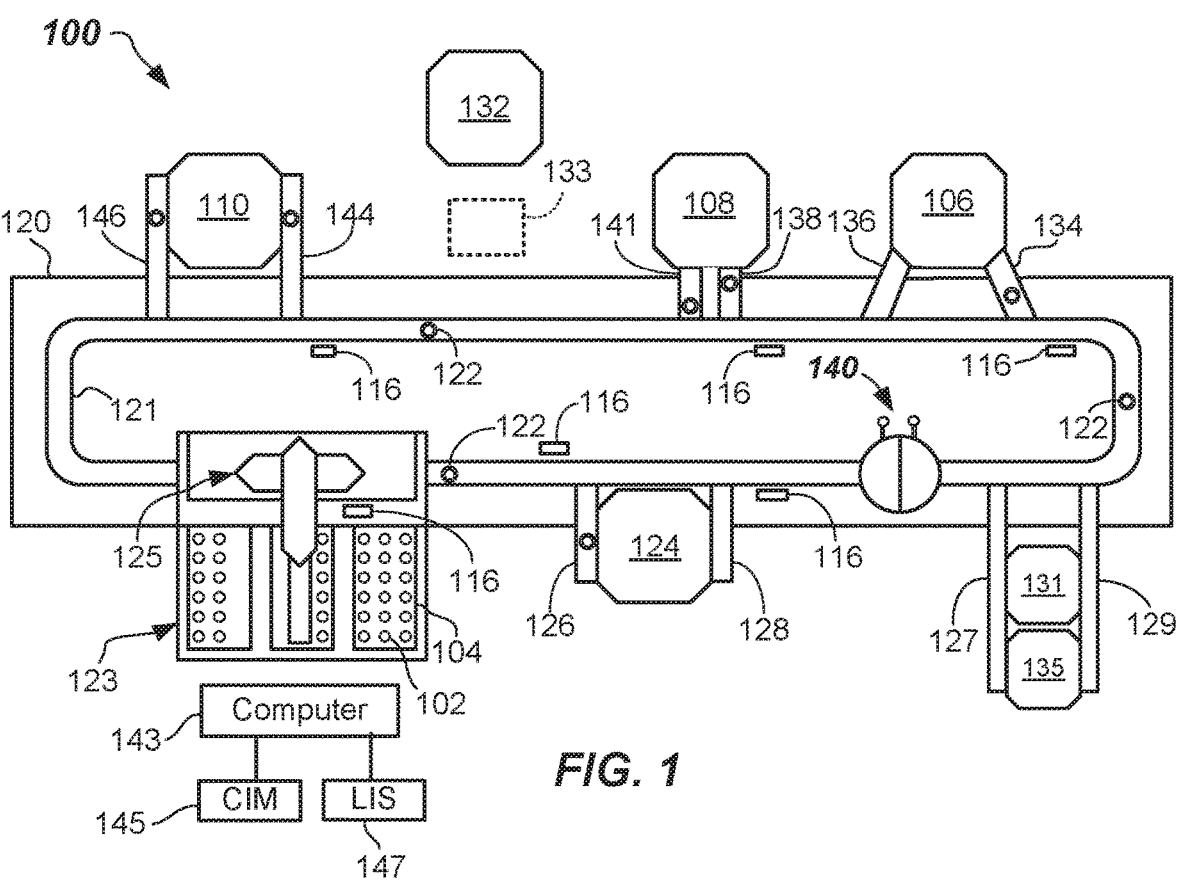
FIG. 1 illustrates a schematic top plan view of an automated specimen testing system including one or more optical characterization apparatus or pre-analytical processing stations and one or more analyzers according to embodiments.

A wide variety of automated chemical analyzers are used to analyze specimens, such as in-patient specimens, for the presence of certain chemicals. Some chemical analyzers employ optical devices to measure optical properties of chemicals or specimens within specimen containers. In some embodiments, light absorption properties of specimens and/or specimen containers may be measured by the optical devices (e.g., imaging devices) within chemical analyzers. In other embodiments, fluorescence and light scattering properties of specimens may be measured by the optical devices. In some embodiments, one or more light sources may illuminate the specimens and optical detectors may measure the light absorption and light scatting properties of specimens resulting from the illumination. These measured optical properties may be analyzed to determine information regarding the content of chemical components of the specimens. The optical imaging may also be used to analyze information about the specimen containers, such as identifying cap color and reading barcode labels affixed to the specimen containers.

Full 360 degree views of specimens and specimen containers may be captured by two or more cameras capturing multiple viewpoints of the specimen containers. Images of full 360 degree views of specimen containers may offer many benefits over images captured by a single camera in a fixed location. For example, labels, such as barcode labels, may be on any side of specimen containers and, regardless of their location, are readable by 360 degree images of the specimen containers. In addition, labels may occlude parts of the specimens within the specimen containers. This occluding may make it more difficult for the specimens within the specimen containers to be imaged. However, with multiple viewpoints captured, specimens may be optically analyzed even though portions of the specimens are occluded by labels. For example, a portion of a specimen may be occluded from a first camera, but visible to a second camera.

Specimen imaging devices that capture images of multiple viewpoints of specimen containers require significant space and the placement of optical components may be limited by the structure of the devices. These devices may include conveyance mechanisms, such as tracks and/or robots that move specimen containers into a field of view of all the cameras. Accordingly, the movement of specimen containers has to clear several optical components implemented to capture the several views of the specimen containers. In addition, the imaging location where the specimen containers are imaged should have minimal stray or ambient light that may adversely affect the captured images.

In addition to the foregoing, illuminated backdrops may be associated with each camera and should match the size of vision cones at the respective distances between the cameras and the illuminated backdrops. The distances are constrained by the geometry of the imaging components, which too is restricted as described above. In some embodiments, unique-shaped illuminated backdrops are designed to fit into tightly constrained spaces, which may be costly.

As described above, the space proximate the imaging location may include the conveyance mechanisms, imaging devices, illuminated backdrops, and may also include light shields to block stray light from the imaging location. The high concentration of devices proximate the imaging location may prevent adequate light shields from being implemented proximate the imaging area. Accordingly, the measurements performed by chemical analyzers may be susceptible to the adverse effects of stray light.

The conveyance mechanisms may pass through the field of view of the cameras and may interfere with other optical devices, which limits the position and number of optical devices that may be implemented. Some conveyance mechanisms may be located in the field of view of the cameras, which may limit the minimum viewing distances of the cameras.

Embodiments of the present disclosure provide improved optical characterization apparatus, systems, and methods for automated testing systems. These and other aspects and features of the disclosure will be described with reference to FIGS. 1-9 herein.

Reference will now be made in detail to the example embodiments of this disclosure, which are illustrated in the accompanying drawings. Wherever possible, the same reference numbers will be used throughout the drawings to refer to the same or like parts throughout the several views. Features of the various embodiments described herein may be combined with each other, unless specifically noted otherwise.

Figure 2:
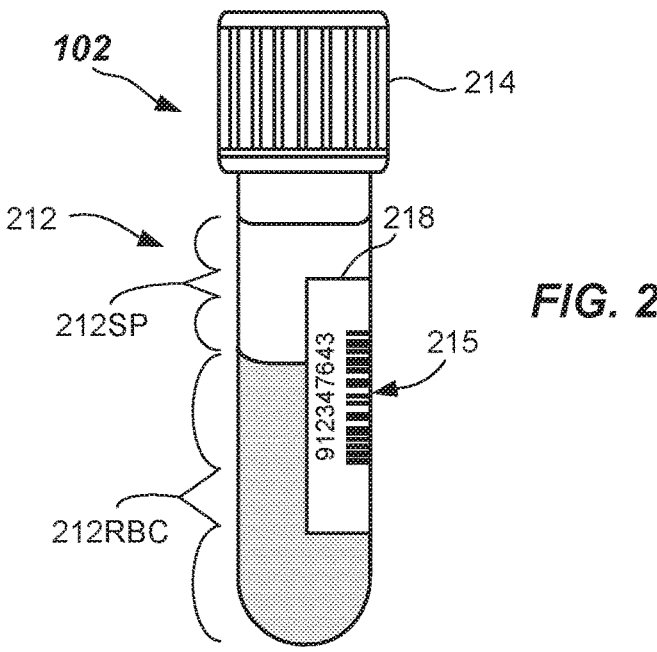
FIG. 2 illustrates a side view of a labeled specimen container including a centrifuged specimen, which may be analyzed for a presence of an interferent according to embodiments.

Reference is now made to FIGS. 1 and 2. FIG. 1 illustrates a top schematic view of an automated specimen testing system 100 configured to automatically pre-process multiple ones of specimen containers 102 (e.g., test tubes, specimen containers, or blood collection tubes—see FIG. 2). FIG. 2 illustrates a side view of a specimen container 102 that has undergone centrifugation at centrifuge 124 to separate out a serum or plasma portion 212SP from a red blood cell portion 212RBC. Specimen containers containing specimens other than blood may be used with the specimen testing system 100. The specimen container 102 may be any generally clear or transparent container, such as a sample cup, cuvette, or other clear glass or plastic container.

The specimen containers 102 may be contained in one or more sample racks 104 prior to analysis by one or more analyzers (e.g., analyzer 106, analyzer 108, and analyzer 110). Specimens 212 may be automatically processed and may be provided to the automated specimen testing system 100 in the specimen containers 102, which may be capped with a cap 214. Each of the specimen containers 102 may be provided with identification information 215, such as a bar code, alphabetic, numeric, or alphanumeric indicia, that may be machine readable by one or more sensors 116 (e.g., barcode readers). The identification information 215 may indicate a patient's identification as well as information concerning the tests or the assay procedures to be accomplished upon the specimen 212 therein, for example. The identification information 215 may be provided on a label 218 adhered to, or otherwise provided on the side of, the specimen container 102. The label 218 may not extend all the way around the specimen container 102, or all along a length of the specimen container 102. Accordingly, although the label 218 may occlude some portion of the specimen 212, some portion of the specimen 212 may still be viewable. In some embodiments, the sample racks 104 may have additional identification information thereon.

Automated specimen testing system 100 may include a base 120 (e.g., a frame or other structure) upon which a conveyor track 121 (which may be a collection of conveyor belts, chains, platforms, or the like) or other suitable conveyance mechanism may be mounted. Conveyor track 121 may transport individual ones of the specimen containers 102 that may be carried on the conveyor track 121 in specimen container carriers 122 (e.g., single specimen carrier pucks or automated carriers including a liner motor). Specimen container carriers 122 may leave from a specimen container load/unload station 123 having the one or more sample racks 104. A robot 125 or the like may be configured to grasp the specimen containers 102 from the sample racks 104 and load the specimen containers 102 into the specimen container carriers 122 on an input lane of the conveyor track 121. The robot 125 may be further configured to remove specimen containers 102 from specimen container carriers 122 on the conveyor track 121 upon completion of testing. Upon being loaded onto conveyor track 121, the specimen containers 102 carried by specimen container carriers 122 may progress to the centrifuge 124 (e.g., an automated centrifuge) and may be diverted to the centrifuge 124 by inflow lane 126 or a robot. After being centrifuged, the specimen containers 102 may exit on outflow lane 128 or by the robot and continue on the conveyor track 121 to an optical characterization apparatus 140.

The optical characterization apparatus 140 may be configured to automatically perform a characterization on the specimen containers 102 and specimens 212 contained in the specimen containers 102. The characterization may include determining a presence of one or more interferents such as hemolysis, icterus, and/or lipemia (hereinafter "HIL") in the serum portions 212S of the specimens 212. The characterization may further include determining the characteristics of the specimen containers 102, such as height and/or diameter of the specimen containers 102, presence and color of the cap 214, tilt of specimen containers 102 in the specimen container carriers 122, and other characteristics. Other characteristics of the specimen 212 and/or the specimen container 102 may be determined by the optical characterization apparatus 140.

An image of the serum or plasma portion 212SP of a specimen 212 may be captured by the optical characterization apparatus 140 to determine whether one or more interferents, such as HIL, are present in the specimen 212. In some embodiments, the image of the serum or plasma portion 212SP may be analyzed by any suitable means to determine the type of HIL interferent that is present. For example, a presence of hemolysis, expressing as a reddish hue in the serum or plasma portion 212SP of the specimen 212 may be determined by any suitable optical imaging analysis. The analysis may further determine an interferent level, such as a hemolytic index. In some embodiments, if a hemolyzed specimen 212 is detected at the optical characterization apparatus 140, the specimen 212 may be sent on to an analytical instrument (e.g., a specialized clinical analyzer, such as a remote analyzer 132) where a precise level of hemolysis can be measured and characterized.

Analysis of the captured image of the specimen 212 may optionally or additionally be used to detect icterus in the serum or plasma portion 212SP of the specimen 212. An icterus interferent may arise, for example, from an excess of bilirubin, the result of decaying red blood cells being converted in the spleen into bilirubin. Levels of bilirubin above 2-3 mg/dl may appear visibly yellowish or brownish in color in the serum portion 212S of specimen 212. These levels of bilirubin may, in particular, adversely affect enzyme-based immunoassays carried out on the analyzers (e.g., analyzers 106, 108, and/or 110).

The icterus detection method may be similar to that for detecting hemolysis. The method may commence with receiving a specimen container 102 in the optical characterization apparatus 140 where one or more images of the specimen 212 is captured. An analysis of the one or more images may be performed to test for the presence of icterus in accordance with the methods described herein below. In some embodiments, the same image(s) that was captured for the hemolysis detection may be used for icterus detection. The analysis may further determine an interferent level, such as an icteric index.

According to another broad aspect, embodiments of the disclosure may optionally or additionally be directed to methods and apparatus used to detect lipemia in a specimen 212. A lipemia interferent, may exhibit a whitish appearance in the serum portion 212S of a specimen 212 and may arise from the presence of excess lipids in the blood. Lipid levels above about 50 mg/dl may interfere with antibody binding in immunoassay testing and may accordingly affect immunoassay results from the automated specimen testing system 100.

The lipemia detection method may be similar to that for detecting hemolysis and icterus. The method may include receiving a specimen container 102 in the optical characterization apparatus 140. One or more images of the specimen 212 may be captured and an analysis of the captured image for the presence of lipemia may be performed. In some embodiments, the same image(s) that was captured for the hemolysis and icterus detections may be used for lipemia detection. The analysis may further determine an interferent level, such as a lipemic index.

Lipemia is a specific sample quality discoloration defect, which may be resolved with special processing before the specimen 212 is tested or analyzed on an analyzer (e.g., analyzer 106, 108, 110). If lipemia is detected, the specimen container 102 may be transferred to a remediation station 131 for further processing to remove or reduce lipids. For example, the remediation station 131 may introduce a solvent or other material to reduce the amount of lipemia. Once this is complete, the specimen 212 can be properly analyzed by one or more of the analyzers (e.g., analyzer 106, 108, 110).

The above analyses may optionally determine an interferent level, such as an index (e.g., hemolytic index, icteric index, lipemic index). "Index" as used herein shall mean a grade given to a particular specimen 212 based upon the determined content of interferent present. The grading scale for observation may range from zero through four (0-4), wherein, zero represents substantially none of the respective interferent, while four represents significant presence of the interferent. Alternately, the scale could be 0-10, 0-20, A-F, or some other range.

In some embodiments, the automated specimen testing system 100 may be able to perform corrective actions without user interaction or additional processing on specimens 212 identified by the optical characterization apparatus 140 as having problems. For example, the routing of a specimen container 102 containing a specimen 112 with an HIL interferent may be removed from the conveyor track 121, such as by being diverted to inflow 127 or by a suitable robot. One or more stations, such as remediation station 131 and/or remediation station 135 may perform additional processing on the specimen 212 as a prerequisite to analysis on one or more analyzers (e.g., analyzer 106, 108, 110). The specimen container 102 may then return to the conveyor track 121 by way of outflow 129 or a robot.

If a specimen 212 is found by the optical characterization apparatus 140 to contain no interferents or is otherwise normal, the specimen container 102 with the normal specimen 212 may continue on the conveyor track 121. The specimen may be analyzed in the one or more analyzers (e.g., analyzer 106, 108, and/or 110) before returning to the specimen container load/unload station 123 for offloading. It should be understood that more or less than three analyzers may be linked by the conveyor track 121 but, for purposes of illustration, three are shown.

The centrifuge 124 and each analyzer 106, 108, 110 may be equipped with robotic mechanisms and/or inflow lanes (e.g., inflow lanes 126, 134, 138, 144) configured to remove specimen container carriers 122 from the conveyor track 121. The centrifuge 124 and each analyzer 106, 108, 110 may also be equipped with and robotic mechanisms and/or outflow lanes (e.g., outflow lanes 128, 136, 141 and 146) configured to reenter specimen container carriers 122 to the conveyor track 121.

Additionally, the remote analyzer 132 may be serviced by the automated specimen testing system 100 even though the remote analyzer 132 is not directly linked to the automated specimen testing system 100. For example, an independent robot 133 (shown dotted) may carry specimen containers 102 containing specimens 212 to the remote analyzer 132 and return them after testing. In some embodiments, the specimen containers 102 may be manually removed and returned. The remote analyzer 132 may test for a hemolysis level, for example. Other testing or processing may be accomplished on the remote analyzer 132.

The automated specimen testing system 100 may include the one or more sensors 116 at one or more locations. Sensors 116 may be used to detect the locations of specimen containers 102 along the conveyor track 121 by reading the identification information 215 (FIG. 2) placed on the specimen containers 102, or like information (not shown) on the specimen container carriers 122. In some embodiments, a distinct RFID chip may be embedded in each specimen container carrier 122 and a conventional RFID reader system may be employed in the tracking operation, for example. Other means for tracking the locations of specimen container carriers 122 may be used, such as proximity sensors.

The load/unload station 123 may include a robot 125 including one or more robot arms or components capable of X and Z, Y or X, Y, and Z motion. The robot 125 may be equipped with a robotic end effector (e.g., clamping hands or fingers) adapted to pick up and place the specimen containers 102 into and out of the specimen container carriers 122 and the sample racks 104. However, any suitable type of robot 125 may be used.

Automated specimen testing system 100 may be controlled by a computer 143, such as a microprocessor-based central processing unit CPU, having memory and suitable conditioning electronics and drivers for the system components. Computer 143 may be housed as part of, or separate from, the base 120 of the automated specimen testing system 100. The computer 143 may operate to control movement of the specimen container carriers 122 to and from the load/unload station 123, the centrifuge 124, optical characterization apparatus 140, and each analyzer 106, 108, 110 carrying out various types of testing (e.g., assay processing). The computer 143 may control the automated specimen testing system 100 according to software, firmware, and/or hardware commands or circuits.

Embodiments of the present disclosure may be implemented using a computer interface module (CIM) 145 that allows for a user to easily and quickly access a variety of control screens and status display screens (now shown). These control and display screens may describe some or all aspects of a plurality of interrelated automated devices (e.g., analyzers 106, 108, 110 within automated specimen testing system 100) used for sample preparation and analysis of specimens 212. The CIM 145 may employ a first display screen (not shown) that is directly linked to a plurality of additional display screens (not shown). The display screens may display information about the operational status of a plurality of interrelated automated devices as well as information describing the location of any specific specimen container 102 as well as a status of tests to be performed on, or being performed on, a specimen 212. The CIM 145 is thus adapted to facilitate interactions between an operator and automated specimen testing system 100. The CIM 145 may include a visual touch screen adapted to display a menu including icons, scroll bars, boxes, and buttons through which the operator may interface with the automated specimen testing system 100. The menu may include a number of function buttons programmed to display functional aspects of the automated specimen testing system 100. The computer 143 may interface with a laboratory information system (LIS) 147 and may receive information concerning specimens 212, patient information, information on tests ordered, and the like from the LIS 147. Further, the computer 143 may report analysis results to the LIS 147.

FIG. 2 illustrates a side view of an embodiment of a specimen container 102 that has undergone centrifugation at centrifuge 124 to separate out a serum or plasma portion 212SP from a red blood cell portion 212RBC. As shown, the label 218 may occlude some of the serum or plasma portion 212SP, so that visualization of the serum or plasma portion 212SP by conventional imaging is difficult. Embodiments disclosed herein account for this occluding without having to rotate the specimen container 102. Thus, analysis for interferents in the specimen 212 may occur as the specimen container 102 stops at the optical characterization apparatus 140 on the conveyor track 121.

Figure 3:
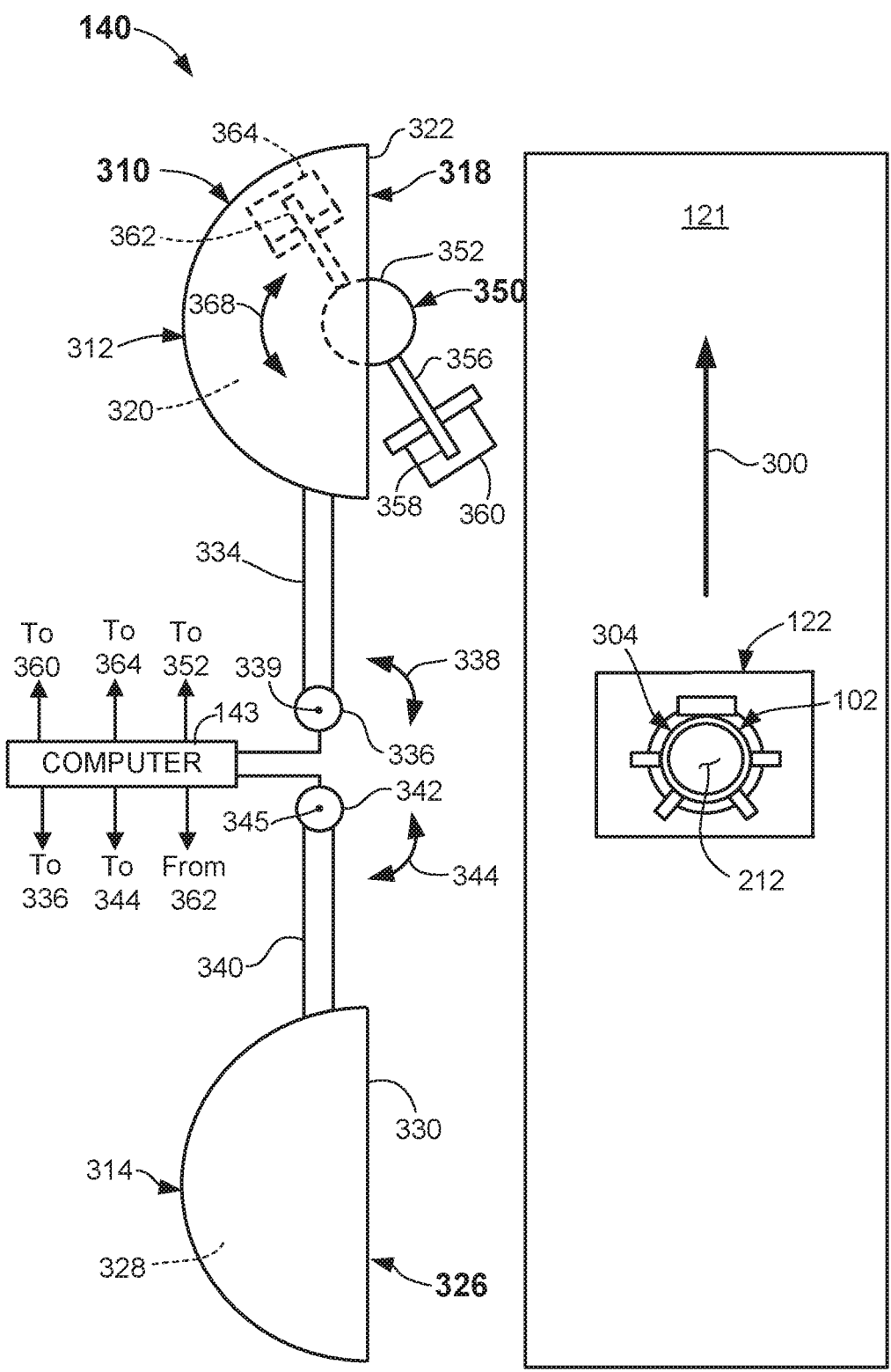
FIG. 3 illustrates a schematic top plan view of an optical characterization apparatus including a moveable hood in an open state according to embodiments.

Reference is now made to FIG. 3, which illustrates a top plan view of an embodiment of an optical characterization apparatus 140 shown in an open state. The optical characterization apparatus 140 may be located adjacent the conveyor track 121 so as to measure or analyze a specimen 212 and/or a specimen container 102 containing the specimen 212. In some embodiments, the optical characterization apparatus 140 may read information, such as labels, located on the specimen container carrier 122 and/or the specimen container 102. The specimen container 102 may be located in the specimen container carrier 122 and may travel in a direction 300 relative to the optical characterization apparatus 140. Other embodiments may enable the specimen container carrier 122 to travel in the direction 300 and/or an opposite direction. Other movement mechanisms may be implemented to move the specimen container carrier 122 or the specimen container 102, such as robotic arms, and the like. The conveyor track 121 may move the specimen container carrier 122 in the direction 300 to position the specimen container 102 into and out of an imaging location 304 where optical imaging may be performed on the specimen container 102 and/or the specimen 212 therein. The imaging location 304 is a location on the conveyor track 121 where the specimen container 102 and/or the specimen 212 therein may be imaged using optical devices described herein.

Analyzing the specimen 212 in the specimen container 102 may include determining or measuring one or more characteristics of the specimen 212, such as the presence of one or more interferent, overall specimen height, height of the red blood cell portion 212RBC, and/or height of the plasma or serum portion 212S. The analyzing may further include determining or measuring physical characteristics of the specimen container 102, such as container height, container diameter, cap type, cap color, whether the specimen container 102 contains a cap, or the like. Determining or measuring a characteristic of the specimen container 102 may further include reading the label 218 (FIG. 2), such as identification information 215 (e.g., a bar code) affixed to or provided on the specimen container 102.

Optical devices and related components that perform imaging on the specimen container 102 and its contents may be located within a moveable hood 310. The moveable hood 310 may be moveable to cover the specimen container 102 and block stray light from the imaging location 304 while imaging is performed on the specimen container 102. The embodiment of the moveable hood 310 depicted in FIG. 3 includes a first hull 312 and a second hull 314. The first hull 312 and the second hull 314 are depicted in FIG. 3 as being semicircular partial cylinders. Other hull shapes and configurations may be used in the optical characterization apparatus 140. The moveable hood 310 depicted in FIG. 3 is shown in an open state, meaning that the first hull 312 and the second hull 314 are separate and not enclosing or otherwise covering the imaging location 304. When the moveable hood 310 is in the open state, the optical characterization apparatus 140 is also referred to as being in an open state.

Figure 4:
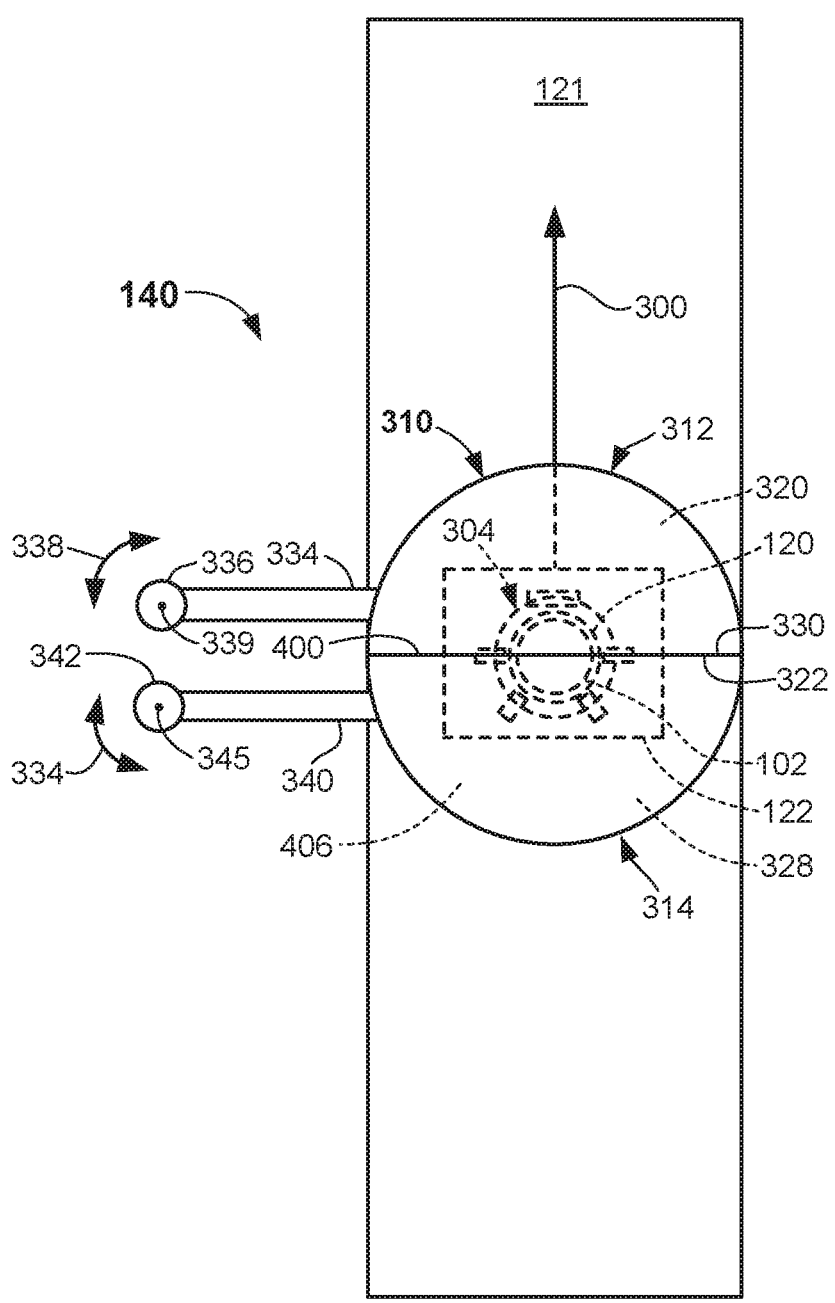
FIG. 4 illustrates a schematic top plan view of an optical characterization apparatus including a moveable hood in a closed state according to embodiments.

The first hull 312 may include a first opening 318 to a first cavity 320. A first surface 322 may be at least partially surrounding the periphery of the first opening 318 to the first cavity 320. The second hull 314 may include a second opening 326 to a second cavity 328. A second surface 330 may be at least partially surrounding the periphery of the second opening 326 to the second cavity 328. The first surface 322 and the second surface 330 may be configured so that they may match or couple to each other to form a closed state of the moveable hood 310 as illustrated in FIG. 4. Stray light may be prevented from passing the interface between the first surface 322 and the second surface 330 when the moveable hood 310 is in the closed state. For example, a seal or other device (not shown) or configuration of the first surface 322 and the second surface 330 may prevent stray light from entering the moveable hood 310 when it is in the closed state. Moreover, a bottom of the hulls 312, 314 may be positioned in close proximity to the track 121 so as to minimize stray light from underneath.

The first hull 312 may be coupled to a first arm 334, which may be coupled to a first actuator 336. The first actuator 336 may pivot the first hull 312 along an arcuate path parallel to a first arc 338 centered about a central axis 339 of the first actuator 336. The second hull 314 may be coupled to a second arm 340, which may be coupled to a second actuator 342. The second actuator 342 may pivot the second hull 314 along an arcuate path parallel to a second arc 344 centered about a central axis 345 of the second actuator 342. Thus, the first hull 312 and second hull 314 may be caused to travel horizontally to the closed state.

Imaging devices and/or analysis equipment may be located within and/or affixed to the first hull 312 and/or the second hull 314. The embodiment depicted in FIG. 3 includes imaging equipment 350 affixed to the first hull 312. As described herein, the imaging equipment 350 may perform imaging on the specimen container 102 and/or the specimen 212 therein. The imaging equipment 350 may include an optical actuator 352 coupled to the first hull 312, such as to an interior thereof. Optionally, the actuator 352 may be coupled to an outside of the first hull 312 or to the second hull 314. The optical actuator 352 may be coupled to one or more optical support arms and may cause the one or more optical support arms to rotate to predetermined positions. An optical support arm 356 is depicted in FIG. 3 as being coupled to the optical actuator 352, and extending radially from the optical actuator 352. The optical support arm 356 may include a first end 358 with a first optical device 360 coupled thereto. The optical support arm 356 may also include a second end 362 with a second optical device 364 coupled thereto (shown dotted in FIG. 3).

The first optical device 360 may be a backlight or other illumination device and the second optical device 364 may be an imaging device, or vice versa. Thus, in some embodiments, backlighting of the imaging location 304 is provided when in the closed state. In some embodiments, the imaging device may be paired with a front illumination component for front illuminating a specimen container and/or specimen therein located at the imaging location 304. Imaging devices include linear optical sensors, line scanners, cameras, barcode readers, telecentric cameras, two-dimensional image capturing devices, single point (scalar) optical sensors, such as photodiodes photoelectric sensor arrays, CCD sensors, CMOS sensors, linear arrays of photodetectors, or any other device that converts light into image data.

The illumination device(s) may include illuminated backdrops or other illumination device(s) that may emit light having different intensities and wavelengths. The illumination device(s) may comprise one or more colored light sources, such as red (R), green (G) and blue (B) light sources, such as RGB light emitting diodes (LEDs). Optionally, the illumination device(s) may comprise one or more lasers. Optionally, the illumination devices may comprise white light (WL) sources and/or infrared (IR) or near IR (NIR) sources. The illumination devices may comprise light panels including combinations of two or more R, G, B, WL, IR, and/or NIR sources. In some embodiments, the illumination devices may provide a changeable illumination pattern. Such a feature may be realized using an LCD mask, a two-dimensional array of light sources, a thin film transistor (TFT), or other display. The changeable illumination pattern may be controlled by the computer 143 to implement multiple illumination configurations, enhancing the information content available for further processing. Other optical devices may be implemented in the optical characterization apparatus 140.

The optical actuator 352 may be a servo device, stepper motor, or the like that is configured to rotate the optical support arm 356 so as to move the first optical device 360 and the second optical device 364 along a path (e.g., an arcuate path) parallel to an arc 368. In some embodiments, the optical actuator 352 may position the first optical device 360 and the second optical device 364 at one or more predetermined positions relative to the specimen container 102 and/or the imaging location 304. As described in greater detail below, the optical actuator 352 may rotate the first optical device 360 and the second optical device 364 at least partially around the specimen container 102 and/or the imaging location 304 to capture an extended image (e.g., a 360 degree image) of the specimen container 102 and/or the specimen 212. The optical actuator 352 may also position the first optical device 360 and the second optical device 364 at predetermined positions as the first hull 312 and the second hull 314 are moved together. When closed state, the first optical device 360 and the second optical device 364 remain separated a suitable distance to avoid physical contact with the specimen container 102 and/or the specimen container carrier 122.

The computer 143 may control the operation of the imaging equipment 350 and collect and/or process data (e.g., image data) generated by the imaging equipment 350. The computer 143 may be coupled to the optical actuator 352, the first optical device 360, the second optical device 364, the first actuator 336, and the second actuator 342. The computer 143 may provide instructions that relate to the intensity and/or wavelength of light emitted as well as the sequencing of and rotational orientation of image capture. In embodiments including a changeable illumination pattern, the computer 143 may be coupled thereto and may provide instructions relate to the intensity and/or wavelength of light emitted in the changeable illumination pattern. The computer 143 may provide data to the optical actuator 352 causing the optical actuator 352 to rotate to specific angles, which moves the first optical device 360 and the second optical device 364 to specific positions. In the embodiment of the first optical device 360 being an imaging device, the computer 143 may instruct the imaging device to capture images of the specimen container 102 at two or more angular orientations. In embodiments of the second optical device 364 being a backlight, the computer 143 may transmit instructions to the backlight instructing it to turn off or on a specific illumination source at certain times during image capture. The instructions may also control a changeable illumination pattern and backdrop patterns. Other instructions may include light intensity emitted by the backlight and frequency or wavelength (e.g., color) of light emitted by the backlight. In some embodiments, the computer 143 may initiate front lighting and image capture at two or more angular orientations. In some embodiments, the computer 143 may analyze images captured by the imaging device. For example, the computer 143 may analyze image data to determine whether an interferent (e.g., an HIL interferent or clot) is present in the specimen 212, to determine the size (e.g., volume) or location of one or more components of the specimen 212 (or interface locations), and/or to determine the size or type of the specimen container 102.

The computer 143 may further instruct the first actuator 336 and the second actuator 342 to rotate the first hull 312 and the second hull 314, respectively. Accordingly the computer 143 may transmit instructions causing the moveable hood 310 to transition between the open state and the closed state. One or more encoders may be used to provide feedback of position of one or more of the first hull 312 and the second hull 314.

Reference is now made to FIG. 4, which illustrates the moveable hood 310 in a closed state. The closed state of the moveable hood 310 may further refer to the optical characterization apparatus 140 being in a closed state. The optical actuator 352 and components coupled thereto are not illustrated in FIG. 4 for illustration purposes. The closed state of the moveable hood 310 may be achieved by the first actuator 336 rotating clockwise and the second actuator 342 rotating counter-clockwise to bring the first hull 312 and the second hull 314 together over the specimen container 102 or imaging location 304. Specifically, the first surface 322 may be matched to the second surface 330 to create an interface 400 between the first surface 322 and the second surface 330 when the moveable hood 310 is in the closed state. The first surface 322 may be made to contact the second surface 330 in some embodiments. The combination of the first cavity 320 and the second cavity 328 forms an enclosure 406 when the moveable hood 310 is in the closed state. The enclosure 406 is at least a portion of a space proximate the imaging location 304. The interface 400 between the first surface 322 and the second surface 330 may prevent stray and/or ambient light from entering the enclosure 406 and adversely affecting images captured by the imaging equipment 350 (FIG. 3). In the closed state, the enclosure 406 may be provided in close proximity or even in contact with the track 121 to minimize stray light entry from the bottom.

Figure 5:
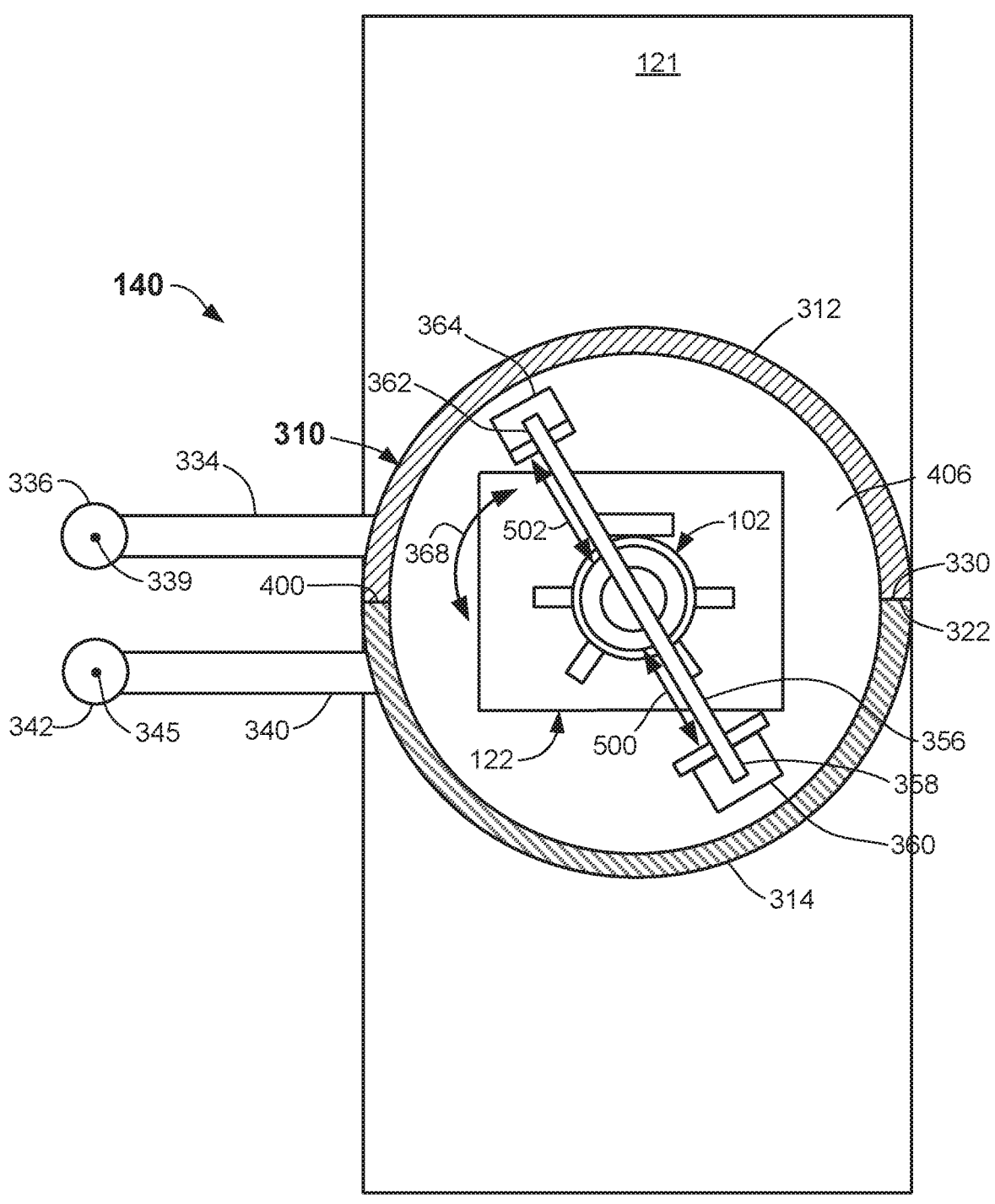
FIG. 5 illustrates a schematic top plan view of an optical characterization apparatus including a cross-sectioned view of a moveable hood in a closed state according to embodiments.
Figure 6:
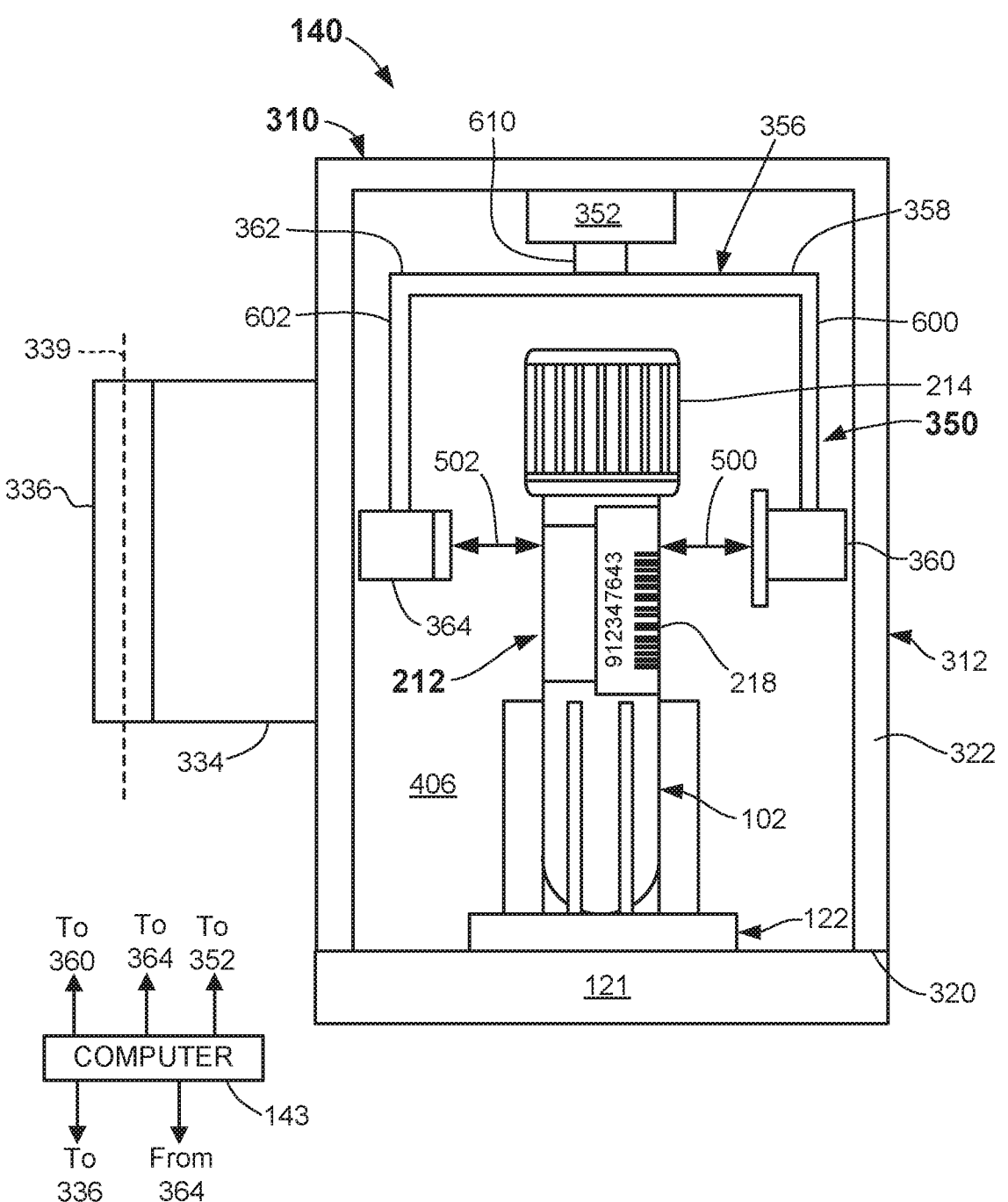
FIG. 6 illustrates a schematic side elevation view of an optical characterization apparatus with a hull removed from a moveable hood according to embodiments.

Reference is now made to FIGS. 5 and 6. FIG. 5 illustrates a top schematic view of an embodiment of the optical characterization apparatus 140 with a cross-sectional top view of an embodiment of the moveable hood 310. FIG. 6 illustrates a schematic side elevation view of an embodiment of the optical characterization apparatus 140 with the second hull 314 removed. The optical actuator 352 (FIG. 3) is not shown in FIG. 5 to better illustrate other components in the enclosure 406. A first distance 500 extends between the first optical device 360 and the specimen container 102 and a second distance 502 extends between the second optical device 364 and the specimen container 102. The first distance 500 and the second distance 502 may remain constant as the first optical device 360 and the second optical device 364 rotate along a path of the arc 368. Thus, multiple views along a 360 degree arc captured by the first optical device 360 and/or the second optical device 364 may maintain constant optical properties as the first optical device 360 and the second optical device 364 rotate around the specimen container 102.

Referring to FIG. 6, a first extension 600 may extend between the first end 358 of the optical support arm 356 and the first optical device 360. A second extension 602 may extend between the second end 362 of the optical support arm 356 and the second optical device 364. The first extension 600 and the second extension 602 may extend vertically as shown, and may enable the first optical device 360 and the second optical device 364 to image predetermined heights of the specimen container 102 and, thus, the specimen 212 therein.

The optical actuator 352 may be coupled to the optical support arm 356 by way of a shaft 610 or other connection. The shaft 610 may have electrically-conductive rings and electrical brushes (not shown) configured to transfer data and/or electrical power between exterior electrical devices and the imaging equipment 350 (FIG. 3). Other suitable means from providing electrical power and data transfer may be provided. In embodiments, data may be transmitted between the computer 143 and the first optical device 360 and the second optical device 364. In some embodiments, image data generated by an imaging device of the first optical device 360 and/or the second optical device 364 may be transmitted wirelessly to an external device. In some embodiments the first optical device 360 and/or the second optical device 364 may contain their own power sources (e.g., batteries).

The optical support arm 356 may rotate the first optical device 360 and the second optical device 362 at least partially around the specimen container 102. During this rotation, the first optical device 360 and/or the second optical device 364 may capture images of the specimen container 102 and/or the specimen 212 during rotation. For example, the first optical device 360 may be a backlight device that illuminates the specimen container 102 and the specimen 212 therein. The illumination may be performed with a specific wavelength spectrum and intensity of light. The second optical device 364 may be an imaging device that captures light having passed through the specimen 212 and the specimen container 102. The captured image may be conveyed to computer 143 and analyzed to determine one or more characteristics of the specimen 212 and/or the specimen container 102.

The first hull 312 and the second hull 314 have been described above as moving in arcuate paths between the open state and the closed state. In other embodiments, the first hull 312 and the second hull 314 may move in other directions. For example, the first hull 312 may be located on a first side of the conveyor track 121 and the second hull 314 may be located on a second side of the conveyor track 121 so the first cavity 320 and the second cavity 328 face each other in the open state. The first hull 312 and/or the second hull 314 may move linearly relative to each other so the first surface 322 and the second surface 330 contact in the closed state. Suitable linear actuators may be used to move the first hull 312 and/or the second hull 314. During such linear motion, the first and second extensions 600, 602 would be positioned in alignment with a length of the track 121 to avoid contact with the specimen container 102 upon linear movement.

Figure 7A:
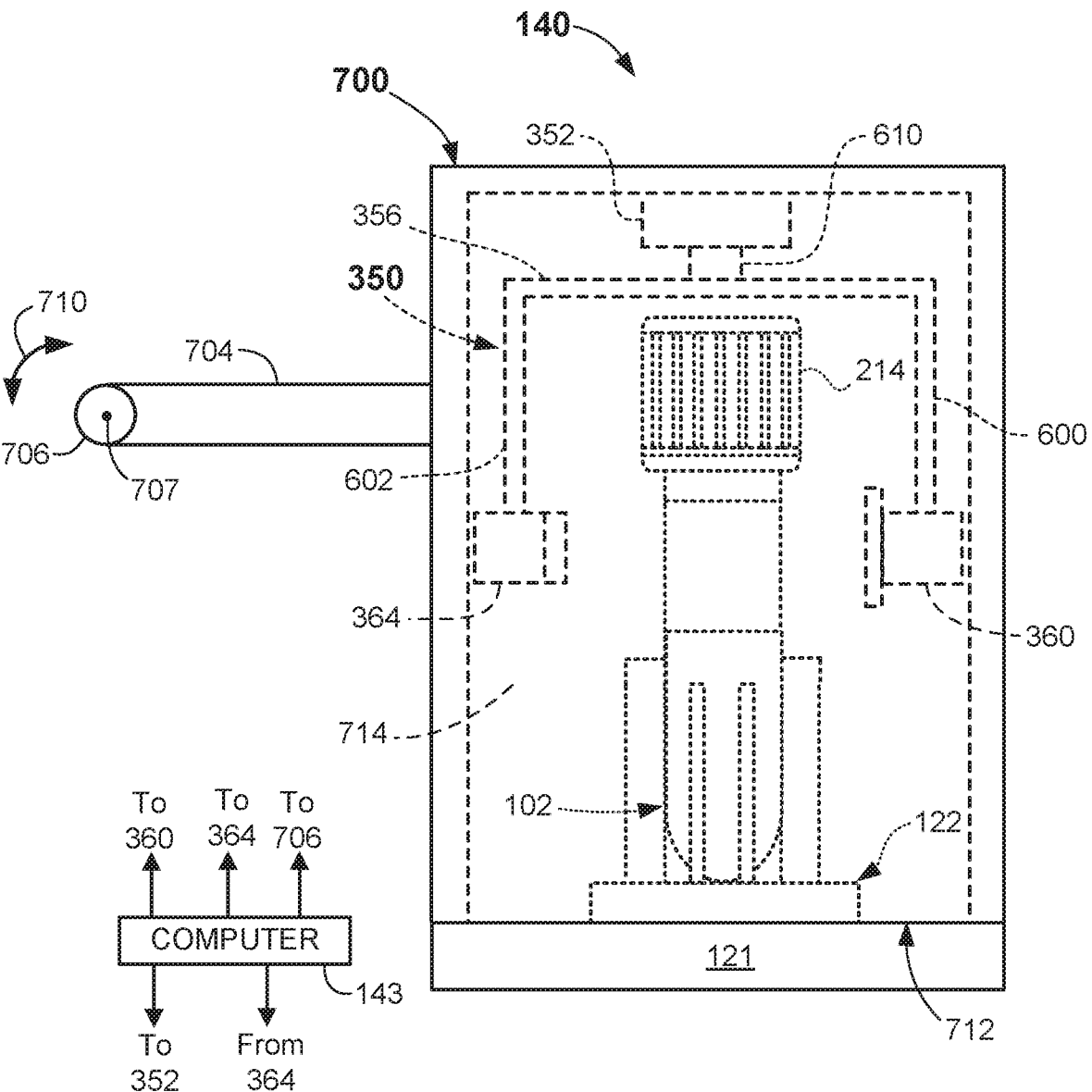
FIG. 7A illustrates a side elevation view of an optical characterization apparatus including a single-piece hood in a closed state according to embodiments.
Figure 7B:
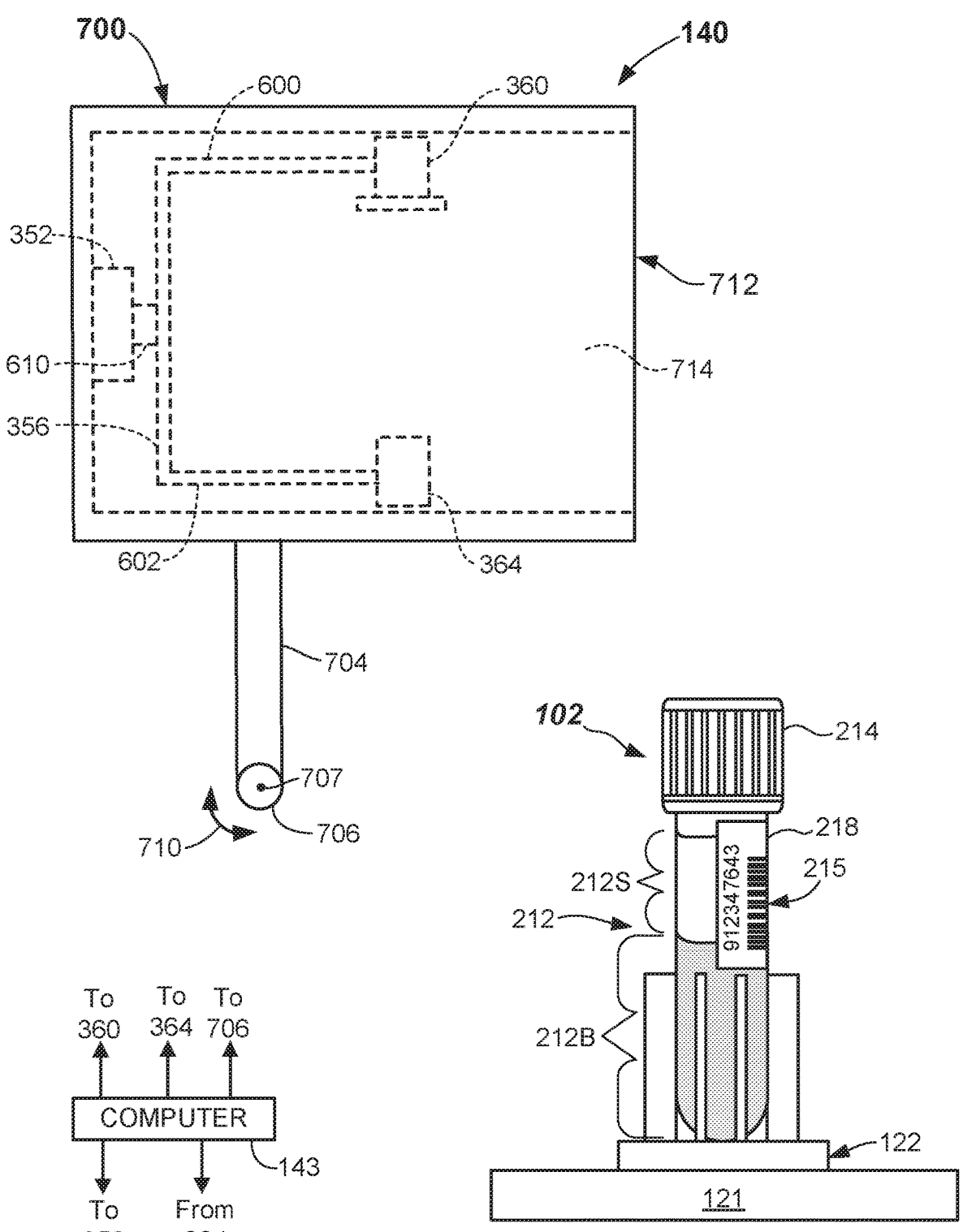
FIG. 7B illustrates the optical characterization apparatus of FIG. 7A with the single-piece hood in an open state according to embodiments.

Reference is now made to FIGS. 7A and 7B. FIG. 7A illustrates a side elevation view of an embodiment of the optical characterization apparatus 140 shown in a closed state. FIG. 7B illustrates an embodiment of the optical characterization apparatus 140 of FIG. 7A shown in an open state. The optical characterization apparatus 140 depicted in FIGS. 7A and 7B includes a single-piece hood 700 coupled to an actuator 706 by an arm 704. A single-piece hood includes a single-piece device, which may be in the form of in inverted cup, that is moveable between a first or closed state that at least partially encloses a specimen container 102 located on the imaging location 304 and a second or open state that does not at least partially enclose a specimen container 102.

The single-piece hood 700 may include an opening 712 at the bottom that opens to an enclosure 714. The opening 712 may be sized and configured to set over a specimen container 102 so that no portion of the specimen container 102 is located within the enclosure 714 when the single-piece hood 700 is in the open state. The opening 712 may further be sized and configured to set over a specimen container carrier 122 so that at least a portion of the specimen container carrier 122 is located within the enclosure 714 when the single-piece hood 700 is in the closed state.

The single-piece hood 700 may transition between the open state and the closed state by movement of the actuator 706. Specifically, the actuator 706 may pivot the single-piece hood 700 about an axis 707, which may be centered in the actuator 706. The actuator 706 may be mechanically coupled to a structure, such as the base 120 (FIG. 1). The computer 143 may transmit signals to the actuator 706 causing the actuator 706 to rotate along an arcuate path of the arc 710. This rotation causes the single-piece hood 700 to transition between the open state and the closed state. Other mechanisms may be employed to move the single-piece hood 700 between the open state and the closed state. The movement of the single-piece hood 700 between the open state and the closed state may be along other paths. For example, the single-piece hood may translate vertically between the open state and the closed state by way of a linear actuator and possibly a linear bearing.

Imaging equipment 350 may be affixed to an interior portion of the single-piece hood 700. The imaging equipment 350 located within the single-piece hood 700 may be the same imaging equipment 350 described above and may communicate with the computer 143 as described above.

Figure 8:
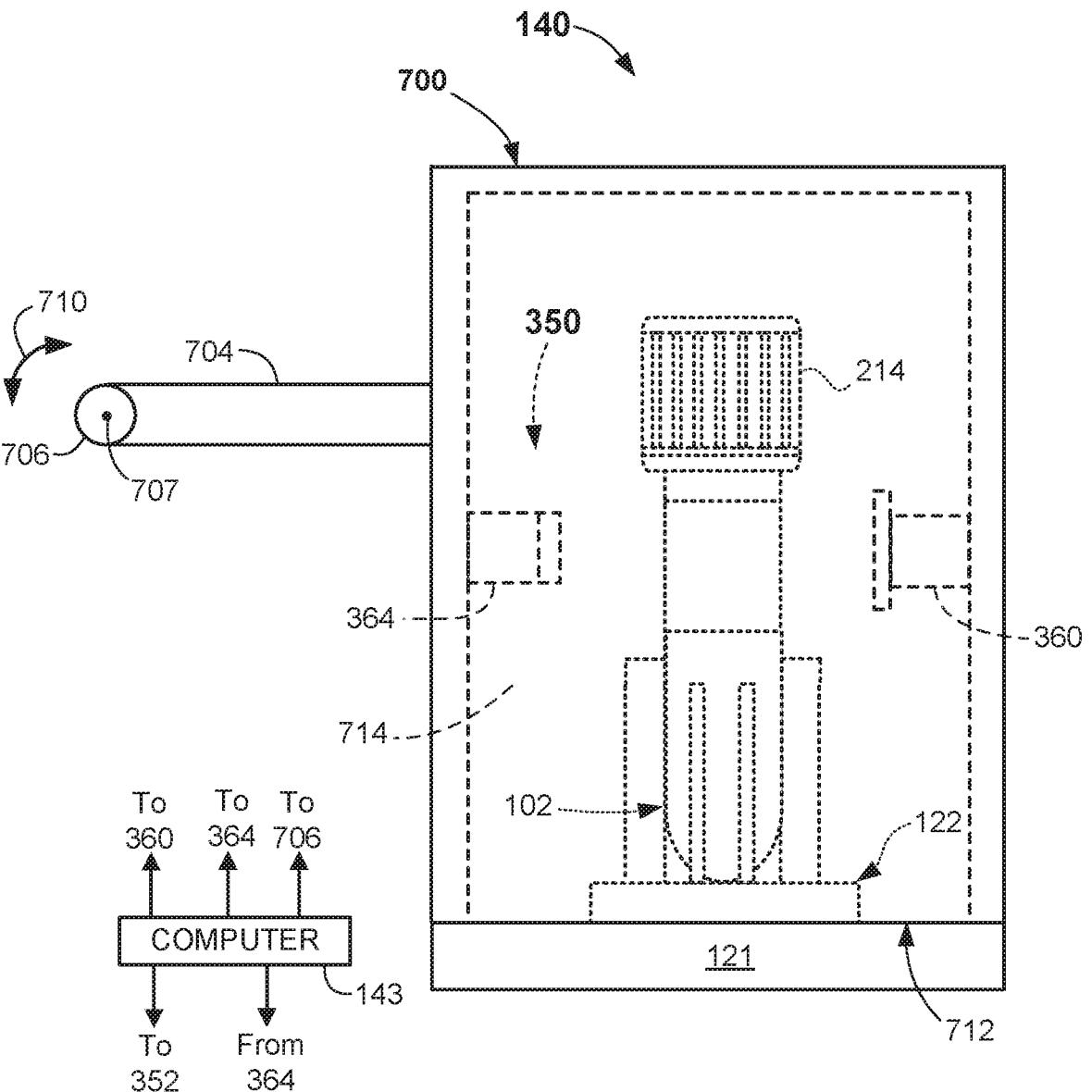
FIG. 8 illustrates an optical characterization apparatus with the imaging devices affixed to a single-piece hood in a closed state according to embodiments.

In optional embodiments, the optical devices 360, 364 may be fixed within or to the moveable hood 310 and/or the single-piece hood 700. For example, as shown in FIG. 8, the optical characterization apparatus 140 may include imaging equipment 350 that is affixed to the single-piece hood 700, such as to an interior portion thereof. Thus, the optical devices 360, 364 move with the single-piece hood 700. Otherwise the movement and operation of the single piece hood 700 is as described in FIG. 7A-7B. Optionally, the clamshell configuration of FIGS. 3 and 4 may be used with the imaging devices 360, 364 affixed to or within the moveable hood 310.

Figure 9:
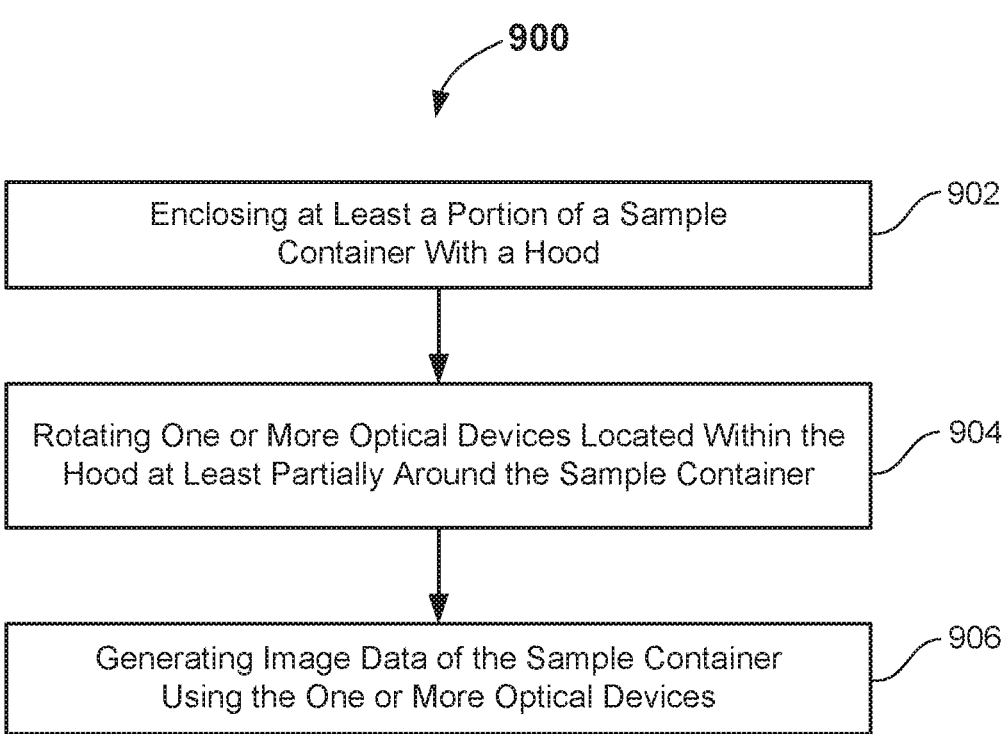
FIG. 9 illustrates a flowchart of a method of measuring a characteristic of a specimen container and/or a specimen in a specimen container according to embodiments.

FIG. 9 illustrates a flowchart of a method 900 of measuring a characteristic of a specimen container and/or a specimen in a specimen container (e.g., specimen container 102). The method 900 may include, in 902, enclosing at least a portion of a specimen container (e.g., specimen container 102) with a hood (e.g., moveable hood 310 or single piece hood 700). The enclosing may be implemented by movement of a multiple piece moveable hood 310 or a single-piece hood 700, for example, as described above.

The method 900 may further include, in 904, rotating one or more optical devices (e.g., first optical device 360 and/or second optical device 364) located within the hood at least partially around the specimen container. The optical devices may be as described above. The "at least partially around" may be, for example, 180 degrees when two imaging devices are used, and may be 360 degrees when one imaging device is used. However, greater than zero degrees and less than 360 degrees may be used. The method 900 may further include, in 906, generating image data of the specimen container 102 using the one or more optical devices (e.g., imaging device and light source). The image data may include one or more images captured at each of multiple angular orientations or even a video image or panoramic image wherein, in each case, the image data may be captured at one or more lighting intensities, exposures, and/or light spectra.

The optical characterization apparatus and methods described herein enable imaging of specimen containers 102 and specimens 212 with fewer physical restraints. For example, mechanisms that move specimen containers are not likely to interfere with optical devices that image the specimen containers. The hoods described herein may provide light shielding from ambient and/or stray light emitted from outside the imaging area without the use of mechanical shutters. Furthermore, the devices and methods described herein may enable multi-orientation (e.g., full 360 degree) imaging with constant distances between the specimen containers 102 and imaging devices. The same applies to backlighting the specimen containers 102 when an optical device described herein is a back illumination source or the like.

Other embodiments of the optical characterization apparatus may include a single imaging device rotatable within the moveable hood 310 and/or the single-piece hood 700.

The foregoing description discloses only example embodiments of the disclosure. Modifications of the above-disclosed apparatus, systems and methods which fall within the scope of the disclosure will be readily apparent to those of ordinary skill in the art. Accordingly, while the present disclosure has been disclosed in connection with example embodiments, it should be understood that other embodiments may fall within the scope of the disclosure, as defined by the claims.

What is claimed is:

1. A method of imaging a specimen container and/or a specimen in the specimen container, comprising:
    transporting the specimen container to an imaging location via a conveyance mechanism extending through the imaging location;
    enclosing at least a portion of the specimen container with a moveable hood at the imaging location, the moveable hood moveable toward and away from the specimen container and movable over the conveyance mechanism;
    rotating one or more optical devices located within the moveable hood at least partially around the specimen container;

generating image data of the specimen container using the one or more optical devices; and transporting the specimen container away from the imaging location via the conveyance mechanism.

2. The method of claim 1, wherein the enclosing the at least a portion of the specimen container with the moveable hood comprises matching a first hull of the moveable hood to a second hull of the moveable hood.

3. The method of claim 2, wherein the matching of the first hull to the second hull comprises moving the first hull to a position wherein the first hull at least partially encloses the specimen container and moving the second hull to a position wherein the second hull at least partially encloses the specimen container.

4. The method of claim 2, wherein the matching of the first hull to the second hull comprises moving the first hull in a first direction and moving the second hull in a second direction, the second direction being opposite the first direction.

5. The method of claim 1, wherein the enclosing at least a portion of the specimen container with the movable hood comprises enclosing at least a portion of the specimen container with a single-piece hood.

6. The method of claim 5, wherein the enclosing at least a portion of the specimen container with the single-piece hood comprises moving the single-piece hood to at least partially enclose the specimen container.

7. The method of claim 1, wherein the generating image data comprises generating image data of the specimen within the specimen container.

8. The method of claim 1, wherein the rotating one or more optical devices comprises rotating an imaging device at least part way around the specimen container.

9. The method of claim 1, wherein the rotating one or more optical devices comprises rotating a barcode reader at least part way around the specimen container.

10. The method of claim 1, wherein the rotating one or more optical devices comprises rotating one or more light detectors at least part way around the specimen container.

11. The method of claim 1, wherein the rotating one or more optical devices comprises rotating an imaging device and an illumination device at least part way around the specimen container.

12. The method of claim 1, wherein the rotating the one or more optical devices located within the moveable hood comprises rotating the one or more optical devices at least partially around the interior of the moveable hood via an actuator coupled between the moveable hood and the one or more optical devices.

13. A method of imaging a specimen container and/or a specimen in the specimen container, comprising:

enclosing at least a portion of the specimen container with a moveable hood;

rotating one or more optical devices located within the moveable hood at least partially around the specimen container; and generating image data of the specimen container using the one or more optical devices;

wherein the enclosing comprises matching a first hull of the moveable hood to a second hull of the moveable hood; and wherein the matching comprises moving the first hull to a position wherein the first hull at least partially encloses the specimen container and moving the second hull to a position wherein the second hull at least partially encloses the specimen container.

14. The method of claim 13, wherein the generating image data comprises generating image data of the specimen within the specimen container.

15. The method of claim 13, wherein the rotating one or more optical devices comprises rotating a barcode reader at least part way around the specimen container.

16. The method of claim 13, wherein the rotating one or more optical devices comprises rotating one or more light detectors at least part way around the specimen container.

17. The method of claim 13, wherein the rotating one or more optical devices comprises rotating an imaging device and an illumination device at least part way around the specimen container.

18. A method of imaging a specimen container and/or a specimen in the specimen container, comprising:

enclosing at least a portion of the specimen container with a moveable hood;

rotating one or more optical devices located within the moveable hood at least partially around the specimen container; and generating image data of the specimen container using the one or more optical devices;

wherein the enclosing comprises matching a first hull of the moveable hood to a second hull of the moveable hood; and wherein the matching comprises moving the first hull in a first direction and moving the second hull in a second direction, the second direction being opposite the first direction.

19. The method of claim 18, where the rotating one or more optical devices comprises rotating an imaging device at least part way around the specimen container.

20. The method of claim 18, wherein the rotating one or more optical devices comprises rotating a barcode reader at least part way around the specimen container.

21. The method of claim 18, wherein the rotating one or more optical devices comprises rotating an imaging device and an illumination device at least part way around the specimen container.

* * * * *